United States Patent [19]

Hardy

[11] Patent Number: 5,735,812
[45] Date of Patent: Apr. 7, 1998

[54] WATER SOLUBLE WOUND DRESSING MATERIALS

[75] Inventor: Craig J. Hardy, Keighley, United Kingdom

[73] Assignee: Johnson & Johnson Medical, Inc., Arlington, Tex.

[21] Appl. No.: 204,024

[22] Filed: Feb. 28, 1994

[30] Foreign Application Priority Data

Mar. 3, 1993 [GB] United Kingdom ............... 9304309

[51] Int. Cl.$^6$ ............................................ A61F 13/00
[52] U.S. Cl. ............................................ 602/43; 602/50
[58] Field of Search ................................. 602/41, 42, 43, 602/46, 48, 50; 604/368

[56] References Cited

U.S. PATENT DOCUMENTS

| | | | |
|---|---|---|---|
| 3,681,489 | 8/1972 | Ford et al. | 264/307 |
| 4,364,929 | 12/1982 | Sasmor et al. | 424/80 |
| 4,393,048 | 7/1983 | Mason, Jr. et al. | 424/132 |
| 4,524,064 | 6/1985 | Nambu | 424/81 |
| 4,793,337 | 12/1988 | Freeman et al. | 128/156 |
| 4,909,244 | 3/1990 | Quarfoot et al. | 128/156 |
| 5,106,629 | 4/1992 | Cartmell et al. | 602/48 |
| 5,115,801 | 5/1992 | Cartmell et al. | 602/48 |
| 5,156,601 | 10/1992 | Lorenz et al. | 602/46 |
| 5,204,110 | 4/1993 | Cartmell et al. | 602/48 |
| 5,306,504 | 4/1994 | Lorenz | 602/48 |

FOREIGN PATENT DOCUMENTS

| | | |
|---|---|---|
| 0 095 892 | 12/1983 | European Pat. Off. |
| 0 099 758 | 1/1984 | European Pat. Off. |
| 0 227 955 | 8/1987 | European Pat. Off. |
| 0 344 913 | 6/1989 | European Pat. Off. |
| 0 439 339 A3 | 7/1991 | European Pat. Off. |
| 0 459 378 A1 | 12/1991 | European Pat. Off. |
| 0 532 275 A1 | 3/1993 | European Pat. Off. |
| 0 568 368 A1 | 11/1993 | European Pat. Off. |
| 906 911 | 9/1962 | United Kingdom. |
| 1 379 158 | 1/1975 | United Kingdom. |
| WO 90/01954 | 8/1990 | WIPO. |

*Primary Examiner*—Corrine M. McDermott
*Assistant Examiner*—Mark Bockelman

[57] ABSTRACT

The invention provides water soluble wound dressing materials comprising from 5% to 50% of an alginate ester of a $C_1$–$C_6$ polyhydric alcohol; from 50% to 95% of a humectant consisting of one or more $C_1$–$C_6$ monohydric or polyhydric alcohols; and from 0% to 30% of water, the percentages being calculated by weight based on the weight of the material when anhydrous. The preferred alginate ester is propylene glycol alginate (PGA). The materials dissolve in water at temperatures below 40° C. The materials are normally produced in the form of soft, conformable, wound-friendly films. The materials may also comprise medicaments or antiseptics.

11 Claims, No Drawings

WATER SOLUBLE WOUND DRESSING MATERIALS

The present invention relates to a water soluble material suitable for application to the surface of a wound as or in a wound dressing.

The use of biopolymers as the wound contacting layer of wound dressings is well known in the art. Biopolymers may be made absorbent, biocompatible and resorbable, thereby assisting wound healing. In addition, several biopolymers such as collagen, chitin, chitosan and alginates have been shown actively to assist wound healing by chemotaxis. Some biopolymers also exhibit a haemostatic effect.

Among the preferred biopolymers for wound healing applications are the alginates. This is on account of the abundance of alginates, their well-understood physico-chemical properties and their proven chemotactic effect on wound healing. The alginates may be applied to the wound in a water-soluble form, for example by dusting sodium alginate powder onto the wound. Alternatively, the alginate may be applied as insoluble calcium alginate, or as an insoluble and water-swellable mixture of sodium alginate and calcium alginate. The soluble or insoluble alginate may be in the form of fibres, a fleece, a gauze or a film. It may be attached to other elements of a wound dressing such as an absorbent layer, a semipermeable or impermeable backing layer, and/or an adhesive-coated layer. Typical such alginate fleeces and wound dressings incorporating them are disclosed, for example, in GB-A-1379158, GB-A-906911, U.S. Pat. No. 4,793,337, WO 90/01954, U.S. Pat. No. 4,393,048, EP-A-0227955, EP-A-0099758, EP-A-0344913 and EP-A-0459378.

For many applications a continuous film of alginate is desirable as the wound contacting layer. Such a film presents a uniform contacting surface to the wound and helps to exclude bacteria from the wound. Continuous films are also easier to remove without disrupting the wound bed.

Alternatively, the film may be perforated or reticulated to allow passage through the film of heavy flows of exudate from the wound while remaining easily removable.

In order to be useful, the alginate film should preferably be strong, elastic, highly conformable, inexpensive, absorbent and sterilizable by gamma irradiation. Preferably, the alginate film should contain a high proportion of humectants such as glycerol so as to maintain a moist wound surface.

Hitherto, no alginate-containing film has provided the optimum combination of properties for use as a wound dressing. For example, anhydrous films of calcium and/or sodium alginate have been suggested for this application. However, the anhydrous films may incorporate only up to about 10% by weight of humectants, which is insufficient for effective moisturising of the wound surface. Moreover, the high alginate content of the anhydrous films makes then relatively expensive. The amount of humectant incorporated in the films may be increased by incorporating water as well, and this also reduces the cost of the film. However, incorporation of water weakens the films. Films containing water present storage problems because they dry out in air. Films containing substantial amounts of water cannot be sterilized by gamma-irradiation.

EP-A-0459378 (FIDIA S.p.A) discloses films containing between 1% and 7.5% by weight of one or more alkali metal alginates such as sodium alginate, from 0.1% to 5% of an alkali earth alginate such as calcium alginate, from 0.1% to 10% of a polyhydric alcohol and from 0.05% to 10% of a hydrophilic polymer such as hyaluronic acid, the balance of the composition being mainly water. The film is made by extruding a solution containing sodium alginate into a calcium chloride bath, where insoluble calcium alginate is formed. The resulting film cannot be sterilised by gamma-irradiation and must be stored under a glycerol/water solution to prevent it from drying out.

EP-A-0095892 (Nippon Oil Co. Ltd.) discloses perforated wound-covering films that comprise: 1.5–8% by weight of a polyvinyl alcohol (PVA), from 10–85% by weight of a polyhydric alcohol humectant and from 0.2–15% by weight of a water-soluble macromolecular substance other than PVA. The water-soluble macromolecular substance is typically a biopolymer or derivative thereof, or a synthetic polymer, provided that it forms a viscous aqueous solution. Preferred macromolecular substances are pullulan, xanthan gum, tragacanth gum, carboxymethylcellulose, polyacrylic acid, i-carrageenan, λ-carrageenan or propylene glycol alginate (PGA). These wound covering films are inexpensive, moisturising, strong, anhydrous and swellable but not soluble in cold or warm water. The main drawback of these films is that the inclusion of PVA even at low concentrations such as 1.5% results in a film that is stiff and rubbery and insufficiently conformable to make a satisfactory wound dressing. The film that contains both PGA and PVA can provide some of the advantageous wound healing properties of the alginate, but the presence of PVA and the rubbery texture of the film mean that the rate of release of PGA into the wound is very slow.

Accordingly, it is an object of the present invention to provide wound dressing materials that are especially suitable for casting into highly conformable wound covering films, and that provide for rapid release of alginate into the wound bed.

The present invention provides a water-soluble wound dressing material comprising, by weight based on the weight of the material when anhydrous: from 5% to 50% of an alginate ester of one or more $C_1$–$C_6$ polyhydric alcohols; from 50% to 95% of a humectant consisting of one or more $C_1$–$C_6$ monohydric or polyhydric alcohols; and from 0% to 30% of water.

The materials according to the present invention are water-soluble. That is to say, they will dissolve in cold or warm water at temperatures below 40° C.

The preferred alginate ester is propylene glycol alginate (PGA). PGA is manufactured by reacting an alginate and propylene oxide at high temperatures. It is available, for example, from Protan Ltd. under the Registered Trade Mark PROTANAL. The viscosity and degree of esterification of the alginate ester are not critical to the materials of the present invention, but preferably the degree of esterification of the alginate is between 35% and 95%. That is to say, between 35% and 95% of the carboxylate groups of the alginate are esterified with the one or more $C_1$–$C_6$ polyhydric alcohols. The remaining carboxylate groups are normally sodium carboxylate groups.

The esterification of the alginate with a polyhydric alcohol greatly increases the affinity of the alginate for humectants consisting of one or more $C_1$–$C_6$ monohydric or polyhydric alcohols. Larger amounts of such humectants can be incorporated into wound dressing materials based on the alginate esters than can be incorporated into anhydrous sodium or calcium alginate materials. Preferably, the materials according to the present invention comprise from 65% to 90% by weight of the humectant. Polyhydric alcohols are the preferred humectants. Preferably, the humectant comprises propylene glycol or glycerol. Other preferred humectants are sorbitol and mannitol.

The high humectant content of the materials according to the present invention makes them especially suitable for use as or in moisturising wound dressings. Furthermore, the materials containing a high proportion of humectants are relatively inexpensive because the humectant is much less costly than alginate. The use of at least 5% by weight of the alginate ester allows surprisingly strong films to be made without the need to add any reinforcing polymer such as PVA. Preferably the materials according to the present invention contain at least 10% by weight, more preferably more than 15% but less than 25% by weight of the alginate ester.

The affinity of the alginate ester for the humectant means that the above high humectant content can be achieved without the need for a high water content in the wound dressing material. Preferably, the materials according to the present invention contain from 5% to 15% by weight of water and more preferably they contain less than 5% by weight of water. The low water content makes the materials sterilizable by gamma-irradiation and also avoids the problem of the materials drying out by evaporation when they are stored in air. The materials according to the present invention typically absorb moisture from the ambient air until they reach an equilibrium water content of 5%–15% by weight depending on the ambient humidity. Because of this variability in the water content of the films all of the weight percentages given for the components in the materials according to the present invention are based on the weight of the material when anhydrous.

The materials according to the present invention optionally contain up to 5% by weight of dissolved salts. Preferably the dissolved salt content is 2% by weight or less of the composition. The dissolved salts preferably contain sodium chloride and may further comprise other salts in physiologically acceptable concentrations.

The materials according to the present invention preferably also comprise up to 2% by weight of a microbicide such as chlorhexidine or an antibiotic to provide protection against wound infection.

The materials according to the present invention preferably also comprise up to 25% by weight of one or more substances that are pharmacologically active to promote wound healing. These substances may comprise molecules such as cytokines and/or biopolymers such as collagen or chitin that have been shown to be effective at promoting wound healing.

The wound dressing materials according to the present invention may be prepared in any convenient physical form, such as a continuous or perforated film, a web, a foam or a fleece of woven or nonwoven fibres. Preferably the material is prepared as a continuous or perforated film.

The wound dressing materials according to the present invention may be prepared in straightforward fashion by mixing together the ingredients with an additional amount of water (up to 50% by weight) to form a gel, casting or extruding the gel in the desired shape and drying the gel at about 80° C. to produce the desired wound dressing material. A further advantage of the wound dressing materials according to the present invention is that relatively little water needs to be evaporated during the manufacturing process in comparison with the manufacture of anhydrous sodium or calcium alginate wound dressings.

Specific embodiments of wound dressing materials according to the present invention will now be described further, by way of example.

EXAMPLE 1

A continuous wound-covering film is prepared as follows. First, 4 g of propylene glycol alginate (PGA) is dissolved in a mixture of 12.5 g of propylene glycol and 12.5 g of glycerol. The PGA is PROTANAL Ester PVH-A, available from Protan Ltd. The degree of esterification is 55–65% and the viscosity of a 1% aqueous solution of the PGA is 1400±200 mPaS.

The above solution is mixed with a solution of 0.45 g of sodium chloride in water to form a gel. The gel is spread by a knife onto a casting roller in a layer approximately 2 mm thick and dried in air at 80° C. for 90 minutes. The water content of the film immediately after drying is less than 5% by weight, increasing to an equilibrium value of about 10% by weight on standing in the atmosphere.

EXAMPLE 2

A continuous wound-covering film is prepared as in Example 1, but with replacement of the 4 g of PROTANAL Ester PVH-A by 6 g of PROTANAL Ester CF. The latter is a PGA having a degree of esterification of 83% and a viscosity (1% aqueous solution) of 20±5 mPaS.

The films obtained in Examples 1 and 2 both show excellent strength, conformability and softness. The high level of humectant in the films makes them effective moisturising wound dressings. The films are very pleasant to handle and are stable in air. No leaching of the humectants is visible when the films are sterilized by gamma-irradiation. Little significant difference in properties is observed between the films of Examples 1 and 2.

The above examples are intended solely for the purpose of illustration. Many other wound dressing materials falling within the scope of the accompanying claims will be apparent to the skilled reader.

I claim:

1. A wound dressing comprising a water-soluble material which comprises, by weight based on the weight of the material when anhydrous:

from 5% to 50% of an alginate ester of one or more $C_1$–$C_6$ polyhydric alcohols; and from 50% to 95% of a humectant consisting of one or more $C_1$–$C_6$ polyhydric alcohols.

2. The water-soluble wound dressing of claim 1, wherein the alginate ester comprises propylene glycol alginate.

3. The water-soluble wound dressing of claim 1, wherein the degree of esterification of the alginate ester is from 35% to 95%.

4. The water-soluble wound dressing of claim 1, wherein the humectant is selected from the group consisting of glycerol and propylene glycol.

5. The water-soluble wound dressing of claim 1 wherein the material contains from 10% to 25% by weight based on the weight of the material when anhydrous of the alginate ester.

6. The water-soluble wound dressing of claim 1, wherein the material contains from 65% to 90% by weight based on the weight of the material when anhydrous of the humectant.

7. The water-soluble wound dressing of claim 1, wherein the material contains from 5% to 15% by weight of water.

8. The water-soluble wound dressing according to claim 1, further including from 0% to 25% by weight based on the weight of the material when anhydrous of one or more substances that are pharmacologically active to promote wound healing.

9. The water-soluble wound dressing of claim 8 wherein the said one or more substances that are pharmacologically active to promote wound healing are selected from the group consisting of cytokines and biopolymers other than alginates.

10. The water-soluble wound dressing of claim 1, further including from 0% to 2% by weight based on the weight of the material when anhydrous of an antimicrobial substance.

11. The water-soluble wound dressing of claim 1 in the form of a continuous or perforated film.

* * * * *